(12) United States Patent
Coleman et al.

(10) Patent No.: US 7,980,722 B2
(45) Date of Patent: Jul. 19, 2011

(54) LIGHT ATTACHMENT FOR INSPECTION TOOL

(75) Inventors: Edward S. Coleman, Ridgefield, CT (US); Qiu Jianping, Hangzhou (CN)

(73) Assignee: Ullman Devices Corporation, Ridgefield, CT (US)

( * ) Notice: Subject to any disclaimer, the term of this patent is extended or adjusted under 35 U.S.C. 154(b) by 0 days.

(21) Appl. No.: 12/263,519

(22) Filed: Nov. 3, 2008

(65) Prior Publication Data

US 2009/0109662 A1 Apr. 30, 2009

Related U.S. Application Data

(63) Continuation-in-part of application No. 12/174,704, filed on Jul. 17, 2008, now Pat. No. 7,954,972.

(60) Provisional application No. 60/954,515, filed on Aug. 7, 2007.

(51) Int. Cl.
*F21V 33/00* (2006.01)
(52) U.S. Cl. .......................................... 362/138; 362/119

(58) Field of Classification Search .................. 362/135, 362/436, 432, 393, 385, 287, 396, 119, 128, 362/296.09, 311.11
See application file for complete search history.

(56) References Cited

U.S. PATENT DOCUMENTS

| | | | | |
|---|---|---|---|---|
| 695,338 | A * | 3/1902 | Paynter | 362/139 |
| 1,057,820 | A * | 4/1913 | Gernsback | 362/135 |
| 1,426,228 | A * | 8/1922 | Sloane et al. | 362/135 |
| 1,555,658 | A | 9/1925 | Gongaware | |
| 5,458,486 | A * | 10/1995 | Ballard | 433/30 |
| 5,645,706 | A * | 7/1997 | Matsuda | 205/82 |
| 6,698,906 | B1 | 3/2004 | Tally | |
| 7,001,037 | B1 * | 2/2006 | Shiao | 362/109 |
| 7,036,627 | B2 * | 5/2006 | Costa et al. | 181/131 |
| 7,475,998 | B1 * | 1/2009 | Pena | 359/875 |
| 2004/0173498 | A1 | 9/2004 | Lee | |

* cited by examiner

*Primary Examiner* — Julie Shallenberger
(74) *Attorney, Agent, or Firm* — Bachman & LaPointe, P.C.

(57) ABSTRACT

A light assembly for an inspection tool having a mirror, the assembly having a mounting bracket attached to the mirror; a light member attached to the mounting bracket; and a power source for the light member.

17 Claims, 3 Drawing Sheets

LIGHT ATTACHMENT FOR INSPECTION TOOL

CROSS REFERENCE TO RELATED APPLICATION

This application is a continuation-in-part of U.S. patent application Ser. No. 12/174,704 filed Jul. 17, 2008, which claims the benefit of provisional application Ser. No. 60/954,515 filed Aug. 7, 2007.

BACKGROUND OF THE INVENTION

The invention relates to inspection tools and, more particularly, to inspection mirrors such as those that are used by mechanics to view obscured areas of an automobile, and also those which are used by security personnel for example to inspect the underside of automobiles.

Such inspection mirrors allow the user to view areas which would otherwise be difficult or impossible to view. In some instances, such areas are not only obscured from the viewer, but are also dark. In such circumstances, it has been known to position a light member shining parallel to the handle of the device, and onto the mirror to illuminate the area to be viewed. While such an approach does help view the intended area, there is room for improvement in such devices.

It is therefore the primary object of the invention to provide an apparatus to allow better illumination of an area to be inspected.

Other objects and advantages of the invention will appear herein.

SUMMARY OF THE INVENTION

According to the invention, the foregoing objects are attained.

According to the invention, a light attachment is provided for attaching to an inspection tool to illuminate the area to be inspected.

A light assembly for an inspection tool having a mirror, the assembly comprising a mounting bracket attached to the mirror; a light member attached to the mounting bracket; and a power source for the light member.

The mounting bracket is preferably shaped to coincide with the shape of the mirror, preferably round or some other relatively simple shape, and can have two or more clips to hold the bracket to the mirror. A battery for the light member is accessibly stored within the mounting bracket.

With the apparatus according to the invention, light is provided directly on the object to be illuminated, and is not reflected onto the object through the mirror as with prior devices. This provides better illumination and allows more thorough inspection of the object or area to be inspected.

In its broadest sense, the mounting bracket can be attached to the mirror using any method, including glues and adhesives. In addition, the mounting bracket can have a rim which traverses the circumference or edge of the mounting bracket, and a notch through which the handle of the mirror extends when the mounting bracket and mirror are assembled. Further, the rim may have a plurality of radially spaced notches to allow the mirror to be mounted to the mounting bracket in a plurality of different positions.

BRIEF DESCRIPTION OF THE DRAWINGS

A detailed description of preferred embodiments of the invention follows, with reference to the attached drawings, wherein.

DETAILED DESCRIPTION

Figure 1:
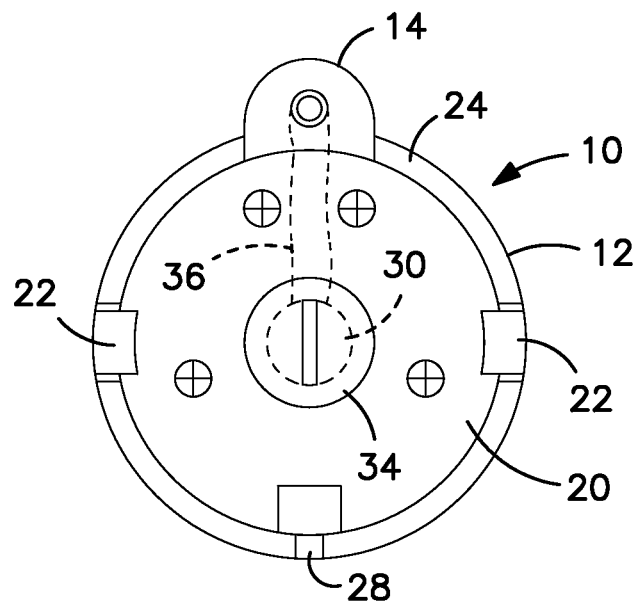
FIG. 1 illustrates an apparatus according to the invention.
Figure 2:
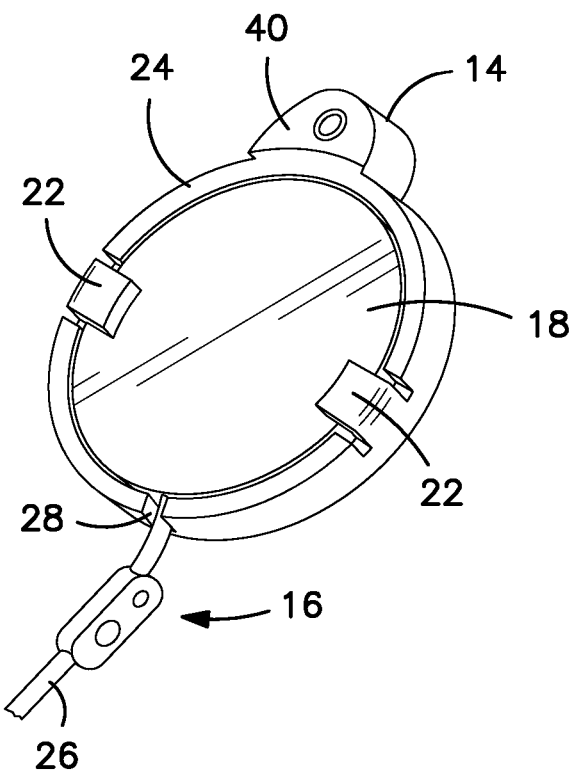
FIG. 2 is a perspective view of the apparatus of the invention installed on an inspection mirror.

FIG. 1 shows an apparatus 10 according to the invention which comprises a mounting bracket generally indicated at 12, and a light member 14 connected to mounting bracket 12. As shown in FIG. 2, mounting bracket 12 is preferably configured for releasable attachment to an inspection mirror tool 16.

Light member 14 can be any suitable light bulb or other light generating device, preferably sufficiently powerful that good illumination can be provided for viewing objects up to several feet from the mirror, from a distance which is also several feet from the mirror. Numerous alternatives are available for the light member as would be well known to a person skilled in this art. Light member 14 can be mounted in mounting bracket 12 in any suitable manner, preferably such that the light bulb itself can be replaced as needed.

Mounting bracket 12 is preferably a structure shaped to fit around the mirror portion 18 of inspection mirror tool 16. FIG. 2 shows a round mirror portion 18, and thus in this embodiment mounting bracket 12 is also substantially round in shape. As shown, mounting bracket 12 can have a body portion 20 sized to be held behind mirror portion 18, and this portion 20 preferably has at least one and preferably at least two clips 22 for snapping past the front edge of mirror portion 18 to hold bracket 12 in place with respect to mirror portion 18. Mounting bracket 12 can also have a forwardly extending lip or rim 24 which is sized to fit around the outer edge or circumference of mirror portion 18, and thereby stabilize mounting bracket 12 relative to mirror portion 18 during use. Inspection mirror tool 16 typically has a handle 26 which can be extended and used to position mirror portion 18 in a desired location to view desired areas or objects. Lip 24 preferably has a notch 28 in lip 24 sized to accept handle 26.

According to the invention, two clips 22 can preferably be positioned at opposite sides of mounting bracket 12 as shown, with light member 14 at a top area of mounting bracket 12, and with notch 28 positioned opposite from light member 12. In this configuration, apparatus mounting bracket 12 can be secured to mirror portion 18 as desired, and light directed along a focal axis of mirror portion 18 also as desired.

Light member 14 can be powered from a battery 30, which can be wired to light member 14, preferably through a switch 32 (FIGS. 3 and 4) to allow light member 14 to be selectively powered off and on. Battery 30 can suitably be stored within a compartment inside mounting bracket 12, and an access door 34 can be provided in mounting bracket 12 to allow battery 30 to be accessed and changed as necessary.

Figure 3:
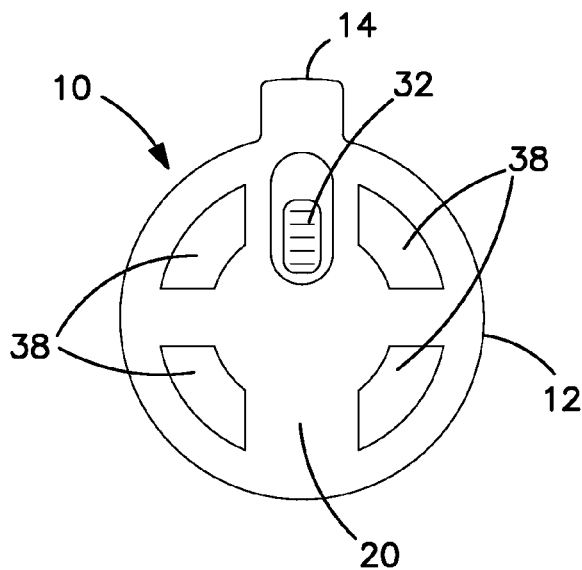
FIG. 3 is a rear view of the apparatus of the present invention.

FIG. 3 shows a rear view of apparatus 10 according to the invention, and shows switch 32 for powering the light on and off. Also, it should be appreciated that mounting bracket 12 in this embodiment is defined by a front wall and a rear wall, and that these walls define the compartment for holding battery 30, as well as the wiring 36 which connects battery 30 and light member 14. FIG. 3 shows one embodiment of the rear wall of apparatus 10, and this rear wall can have a plurality of cutouts 38 which serve to reduce the amount of material required to manufacture mounting bracket 12, which can suitably be injection molded from plastic.

Figure 4:
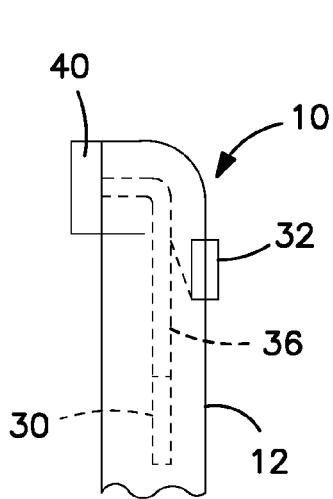
FIG. 4 is a side view of a portion of the apparatus of the invention showing internal wiring of the light member.

FIG. 4 shows a side view and schematically illustrates battery 30, wiring 36 and switch 32 which are used according to the invention to selectively turn light member 14 on and off. FIGS. 2 and 4 show that light member 14 can be surrounded by a housing 40 which extends forwardly beyond mirror 18 and lip 24. This housing 40 serves to protect the light bulb within light member 14 from being damaged by incidental contact with various objects during use of apparatus 10.

Figure 5:
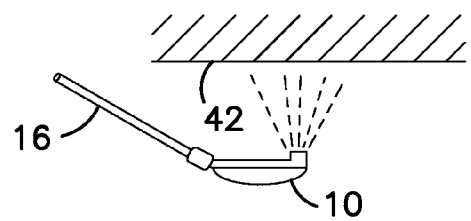
FIG. 5 shows an apparatus according to the invention attached to a mirror and illuminating an otherwise obscured surface.

FIG. 5 shows apparatus 10 secured to an inspection mirror tool 16 and being used to illuminate and view a surface 42. This use of apparatus 10 according to the invention can as indicated above serve to allow inspection of the underside of vehicles, or otherwise obscured areas in an engine compartment and the like.

Figure 6:
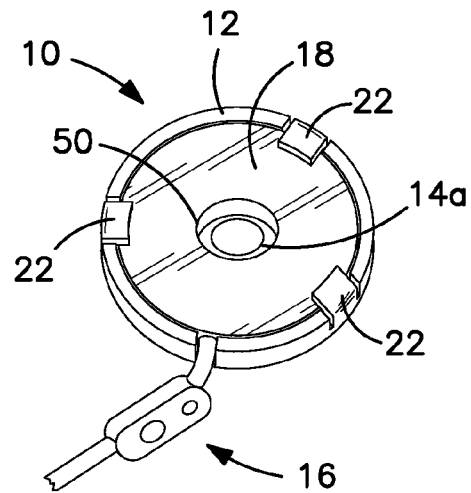
FIG. 6 shows an alternate embodiment of the invention.

FIG. 6 shows an alternate embodiment of apparatus 10 wherein light member 14a is centrally located on holder 12, and mirror portion 18 has a central opening or hole 50 through which light member 14a shines during use. The housing of bracket 12 can be defined by two spaced walls in similar fashion to the embodiment of FIGS. 1-5, with battery and wiring positioned internally, the battery being changeable, and a switch being positioned for powering light member 14a on and off as desired. In this embodiment, while the mirror portion 18 is slightly complicated by the need for central opening 50, the advantage gained by this extra effort is a central location of light member 14a, which serves to more directly and properly illuminate an area to be viewed. Bracket 12 in this embodiment snaps onto and off of mirror portion 18 in similar fashion to the embodiment of FIGS. 1-5.

Figure 7:
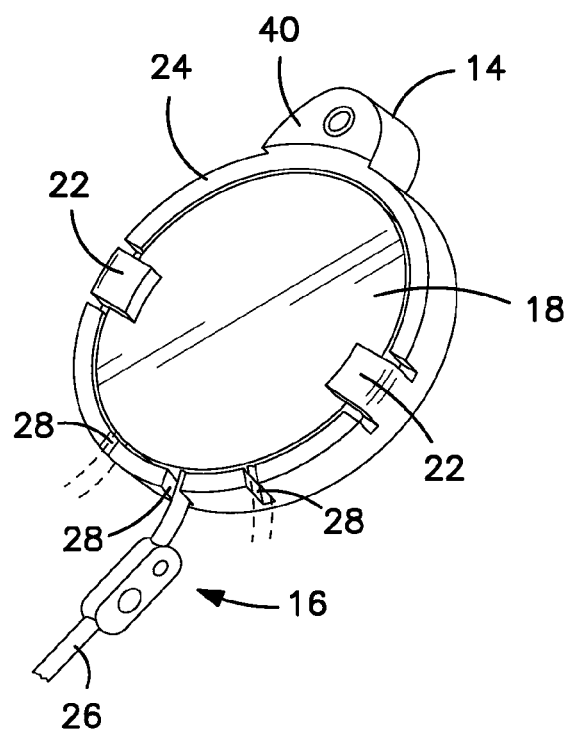
FIG. 7 shows an alternate embodiment of the invention, wherein the mounting bracket has a plurality of notches for accommodating the handle of the mirror in different positions.

Turning to FIG. 7, a further embodiment of the present invention is illustrated, wherein mounting bracket 10 has a plurality of spaced notches 28, in this instance based around circumferential rim 24, to accommodate handle 26 in a plurality of different positions between the mirror and the mounting bracket. In this manner, light member 14 can be positioned in different locations with respect to the handle of the device. It is noted that FIG. 2 shows this embodiment with a round mirror and with notches 28 positioned radically spaced along a portion of the lip accommodating the round mirror. It should be appreciated that this plurality of notches could be utilized in other-shaped mirrors and mounting brackets, well within the broad scope of the present invention.

Figure 8:
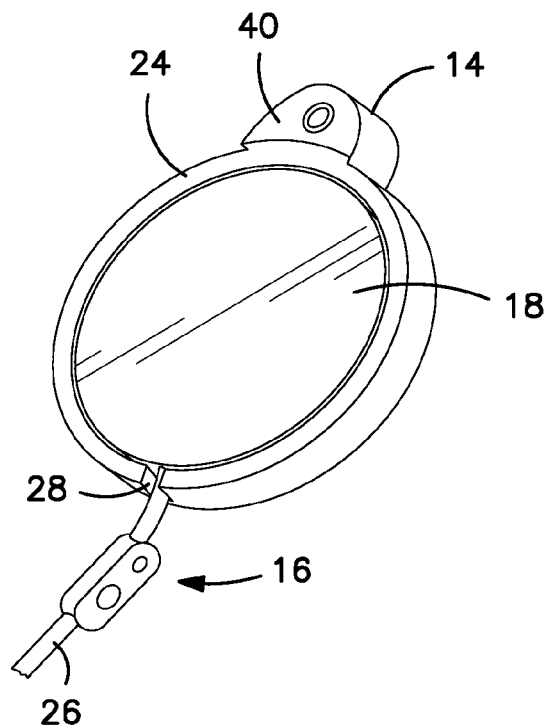
FIG. 8 shows a simplified embodiment of the present invention wherein the mounting bracket is attached to the mirror, for example using glue or some other type of adhesive, without clips.

FIG. 8 shows a further alternate embodiment of the present invention wherein mounting bracket 10 is not releasably connected to the mirror. That is, mounting bracket 10 is configured for other types of attachments to mirror 18, for example involving glue or adhesives for securing mounting bracket 24 to mirror 18. In this embodiment, as well, the mounting bracket and mirror preferably match each other in shape, and could be round, square, triangular, rectangular or the like. It should be appreciated that the simplified structure, while removing the mounting brackets mentioned in earlier embodiments, results in a more permanent structure, but also in potentially reduced costs for the molding of the mounting bracket part, which can now be held in place through either a permanent press fit with the mirror, or with adhesives, or combinations thereof.

It should be appreciated that this description has been provided in terms of a preferred embodiment of the invention, and that various details and aspects of the embodiment described could be modified by a person skilled in the art. The present invention is deemed to include such modifications, and the broad scope of the present invention is not limited by the specific details of this description.

The invention claimed is:

1. A lighted inspection mirror, comprising:
an inspection tool having a mirror and a substantially elongate handle mounted directly to the mirror, the mirror having a reflective front surface and a back surface; and
an enclosed and self-contained light member mounted to the back surface of the mirror, wherein the light member comprises:
an enclosed plastic compartment defining an enclosed inner space and having a rim extending forwardly around at least a portion of an edge of the mirror and at least two clips extending inwardly from the rim over an edge of the mirror, a light bulb and a power source in the enclosed inner space, the light bulb being operatively connected to the power source through wiring in the enclosed inner space.

2. The apparatus of claim 1 wherein the light member is a substantially round structure having at least two clips for holding the light member to the mirror.

3. The apparatus of claim 2, wherein the light member has an edge and a rim along the edge, and wherein the clips extend radially inwardly from the rim.

4. The apparatus of claim 3, further comprising a notch in the rim for accommodating a handle of the mirror.

5. The apparatus of claim 1, wherein the light member has an edge and a rim along the edge, and a plurality of notches in the rim for accommodating a handle of the mirror in different positions.

6. The apparatus of claim 1, wherein the light bulb is positioned along an edge of the light member.

7. The apparatus of claim 1, wherein the light bulb is positioned at a center of the light member.

8. A lighted inspection mirror, comprising:
an inspection tool having a mirror and a substantially elongate handle mounted directly extending from and pivotable relative to the mirror, the mirror having a reflective front surface and a back surface; and
an enclosed and self-contained light member mounted to the back surface of the mirror, wherein the light member comprises:
an enclosed plastic compartment defining an enclosed inner space and having a rim extending forwardly around at least a portion of an edge of the mirror and an extension of at least a portion of the rim extending inwardly from the rim over an edge of the mirror so as to engage the edge of the mirror; a light bulb and a power source in the enclosed inner space, the light bulb being operatively connected to the power source through wiring in the enclosed plastic compartment.

9. The apparatus of claim 8, wherein the light member is adapted for releasable connection to the back surface of the mirror.

10. The apparatus of claim 8, wherein the light member is a substantially round structure and wherein the extension of at least a portion of the rim comprises at least two clips for holding the light member to the mirror.

11. The apparatus of claim 10, wherein the light member has an edge and a rim along the edge, and wherein the clips extend radially inwardly from the rim.

12. The apparatus of claim 11, further comprising a notch in the rim for accommodating the handle of the mirror.

13. The apparatus of claim 8, wherein the light member has an edge and a rim along the edge, and a plurality of notches in the rim for accommodating the handle of the mirror in different positions relative to the light member.

14. The apparatus of claim 8, wherein the light bulb is positioned along an edge of the light member.

15. The apparatus of claim 14, wherein the light bulb is positioned to shine light along a focal axis of the mirror when the light member is attached to the mirror.

16. The apparatus of claim 8, wherein the light bulb is positioned at a center of the light member.

17. The apparatus of claim 16, wherein the mirror has a centrally located opening for light from the light bulb to pass through.

* * * * *

UNITED STATES PATENT AND TRADEMARK OFFICE
CERTIFICATE OF CORRECTION

PATENT NO. : 7,980,722 B2  
APPLICATION NO. : 12/263519  
DATED : July 19, 2011  
INVENTOR(S) : Edward S. Coleman et al.

It is certified that error appears in the above-identified patent and that said Letters Patent is hereby corrected as shown below:

Claim 8 line 3, after handle, delete the words --mounted directly--.

Signed and Sealed this
Twentieth Day of December, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,980,722 B2 | Page 1 of 1 |
| APPLICATION NO. | : 12/263519 | |
| DATED | : July 19, 2011 | |
| INVENTOR(S) | : Edward S. Coleman et al. | |

It is certified that error appears in the above-identified patent and that said Letters Patent is hereby corrected as shown below:

Column 4, line 46 (Claim 8 line 3) after handle, delete the words "mounted directly".

This certificate supersedes the Certificate of Correction issued December 20, 2011.

Signed and Sealed this
Tenth Day of January, 2012

David J. Kappos
*Director of the United States Patent and Trademark Office*